(12) United States Patent
Parota et al.

(10) Patent No.: US 6,298,851 B1
(45) Date of Patent: Oct. 9, 2001

(54) EMERGENCY TRACHEOTOMY APPARATUS

(76) Inventors: Gheorghe Parota, 24 Robertson Rd., East Windsor; Mirabella Magyar, 24 Robertson Rd., Highstown, both of NJ (US) 08520

( * ) Notice: Subject to any disclaimer, the term of this patent is extended or adjusted under 35 U.S.C. 154(b) by 0 days.

(21) Appl. No.: 09/396,572

(22) Filed: Sep. 15, 1999

(51) Int. Cl.⁷ .................................................. A61M 16/00
(52) U.S. Cl. ....................................................... 128/207.29
(58) Field of Search ........................ 128/200.26, 207.14, 128/207.29; 604/96.01, 160, 161, 187, 264, 272; 606/191, 192, 196, 167, 108

(56) References Cited

U.S. PATENT DOCUMENTS

| | | | |
|---|---|---|---|
| Re. 34,086 | * 10/1992 | George | 128/200.26 |
| Re. 36,611 | * 3/2000 | French | 128/207.29 |
| 300,285 | * 6/1884 | Russell . | |
| 1,213,001 | * 1/1917 | Philips . | |
| 3,688,773 | 9/1972 | Weiss . | |
| 3,817,250 | * 6/1974 | Weiss et al. | 128/305 |
| 4,246,897 | * 1/1981 | Muto | 128/207.15 |
| 4,364,391 | * 12/1982 | Toye | 128/305.3 |
| 4,520,810 | * 6/1985 | Weiss | 128/200.26 |
| 4,677,978 | * 7/1987 | Melker | 128/207.14 |
| 4,978,334 | 12/1990 | Toye et al. . | |
| 5,058,580 | * 10/1991 | Hazard | 128/207.15 |
| 5,217,005 | 6/1993 | Weinstein . | |
| 5,507,279 | * 4/1996 | Fortune et al. | 128/200.26 |
| 5,653,230 | * 8/1997 | Ciaglia et al. | 128/207.15 |
| 6,109,264 | * 8/2000 | Sauer | 128/207.29 |

* cited by examiner

Primary Examiner—Glenn K. Dawson
Assistant Examiner—Mital Patel
(74) Attorney, Agent, or Firm—Mathews, Collins, Shepherd, & Gould, P.A.

(57) ABSTRACT

An apparatus for performing emergency tracheotomies having a first cylinder having a distal end in a substantially cone shape and a threaded proximal end. An internal hollow cylinder has a distal end open in a frustum of a cone shape. The hollow interior cylinder receives the first cylinder. An external hollow cylinder has a distal end open in a frustum of a cone shape. The external hollow cylinder is slidably received over the hollow interior cylinder. A ring is slidably received coaxially over the hollow external cylinder. The ring stops the forward movement of the device into a desired position. The device also includes a second cylinder with the distal end in the shape of a hemisphere. After initial inserting of the device into the trachea, the first cylinder is removed and the second cylinder is inserted into the hollow interior cylinder for further insertion of the device without injuring the posterior tracheal wall.

15 Claims, 11 Drawing Sheets

EMERGENCY TRACHEOTOMY APPARATUS

BACKGROUND OF THE INVENTION

1. Field of the Invention

The present invention relates to emergency medical procedures. More particularly, the present invention relates to a device and method for the execution of an emergency tracheotomy.

2. Description of the Related Art

Tracheotomy is an operation for the purpose of relieving an obstruction of the respiratory passage. The device is used to restore the patient's breathing in critical situations when an emergency trauma center is not immediately available. In general, it is necessary to perform a dissection for the insertion of a breathing tube into the tracheal lumen. This procedure requires surgical skills and conventional apparatus are limited to experienced operators.

U.S. Pat. Nos. 3,688,773 and 3,817,250 describe an expandable needle, enlarged in a rear section and tapering to a sharp point for puncturing the skin and tissue of a patient. The sharp end of the needle is used to make the puncture and the entire needle is inserted into the trachea. An air tube is then inserted into the needle, expanding the same, and into the tracheal area to allow the patient to breathe.

Although these prior art devices represent an improvement over the devices previously known, there is a danger that unprotected sharp ends of the needle could be inserted too far into the trachea puncturing the soft posterior wall causing injury and severe complications. Also, the orifice made by the needle does not achieve a circular shape, but an ellipsoidal shape; therefore, the pressure made by the device through a forced dilatation often has the consequence of breaking the inter-cartilaginous membrane.

U.S. Pat. Nos. 4,978,334 describes a device that uses a dilator with a hollow needle. This procedure has the shortcomings that at the moment of the initial penetration through the skin or membrane or when withdrawing the syringe plunger, in order to verify if the tip of the needle is in the tracheal lumen, the use of a hollow needle can result in an obstruction made by fragments of tissues which occur within the needle. The obstruction causes the operator not to be able to evaluate with accuracy the location of the needle since there will not be a positive response. The use of a syringe as an auxiliary element also has the shortcoming that surgical skills are still required and the procedure's time is longer.

Another problem is the complete safe further insertion of the device once it is located within the tracheal lumen. U.S. Pat. No. 5,217,005 ('005) describes a sharp conical tip of a dilator. An annular groove is positioned at the base of the conical tip of the dilator for providing a safety element to avoid the puncturing of the posterior wall of the trachea. A guide wire is used to assist in the guiding of the dilator and the tube into the trachea. However, in spite of the fact that the annular groove becomes flexible after the needle tip is withdrawn, the tip of the dilator is still sharp and it can injure the posterior wall of the trachea in its advancing movement inside the trachea. Also, since the guide wire cannot secure an entirely safe advancement of the dilator's tip, the conic tip is rigid and the guide wire is flexible, a space can appear between the rigid wall of the dilator's conic tip and the curb made by the guide wire at its exit from the dilator. Accordingly, the sharp tip of the dilator's conic portion can scratch the posterior tracheal wall. It is described in the '005 patent that for children and patients with smaller body sizes the height of the conical portion of the dilator can be varied in order to prevent the dilator from injuring the posterior wall of the trachea. However, there is no disclosure in the patent adapting the device for patients with different skin and subcutaneous tissue thickness.

It is desirable to provide a percutaneous device to eliminate the risk of injury which can be used for all patients. Such a device is proposed by the present invention.

SUMMARY OF THE INVENTION

The present invention comprises a percutaneous device for performing of a tracheotomy to enable eliminating of massive bleeding during the procedure, protecting the tracheal wall, particularly the posterior wall, reducing the time of the procedure and increasing the accessibility of use of the device to people having a minimum of training and information.

The device includes a first cylinder having a distal end in a substantially cone shape and a threaded proximal end. An extension extends from the first cylinder and serves as a handle, thereby allowing the insertion of the device into the trachea of a patient. The cylinder includes a longitudinal groove and an auxiliary control rod with a handle. The rod rests into the longitudinal groove and slides along the groove to determine if the first cylinder has been inserted into the trachea lumen.

An internal hollow cylinder has a distal end open and in a frustum of a cone shape. The hollow internal cylinder has a threaded internal and exterior proximal end. The hollow interior cylinder receives the first cylinder and the threaded end of the first cylinder is threaded to the interior threaded end of the hollow interior cylinder. The hollow interior cylinder also has an extension that serves as a handle.

An external hollow cylinder has a distal end open and in a frustum of a cone shape. The external hollow cylinder is slidably received over the hollow interior cylinder. An interior threaded proximal end of the hollow exterior cylinder is threaded to the external threaded hollow interior cylinder. An extension of the hollow exterior cylinder serves as a handle.

The device also includes a second cylinder with the distal end in the shape of a hemisphere and a threaded proximal end. An extension of the second cylinder serves as a handle. After initial inserting of the device into the trachea, the first cylinder is removed and the second cylinder is inserted into the hollow interior cylinder.

A ring is slidably received coaxially over the hollow external cylinder. The ring stops the forward movement of the device into a desired position. A screw is used to hold the ring in the desired position. After the proper positioning of the device into the tracheal lumen of the patient a flexible breathing tube is inserted.

The apparatus proposed by the present invention has the advantages of eliminating completely the need for a syringe, giving access to the people with a minimum of information and training to use it safely and reducing considerably the duration of the entire procedure. Further, the apparatus of the present invention eliminates completely the risk of injury by using a ring for stopping initial penetration of the device and a cylinder with a rounded hemispheric extremity for completing insertion of the device.

The apparatus of the present invention presents a wide application in several domains, for example: auto accidents; military; allergic reactions; inner-tracheal stings by insects which generate massive edema of the larynx when the use of the reanimation "pipe" has become impossible; acute affection of the larynx whenever the situation is created by the severe damaging of the mouth cavity (mandible, harming of the hypo-pharynx, when the use of the reanimation instruments is not possible through the larynx).

The invention will be more fully described by reference to the following drawings.

DETAILED DESCRIPTION OF THE INVENTION

Reference will now be made in greater detail to a preferred embodiment of the invention, an example of which is illustrated in the accompanying drawings. Wherever possible, the same reference numerals will be used throughout the drawings and the description to refer to the same or like parts.

Figure 1A:
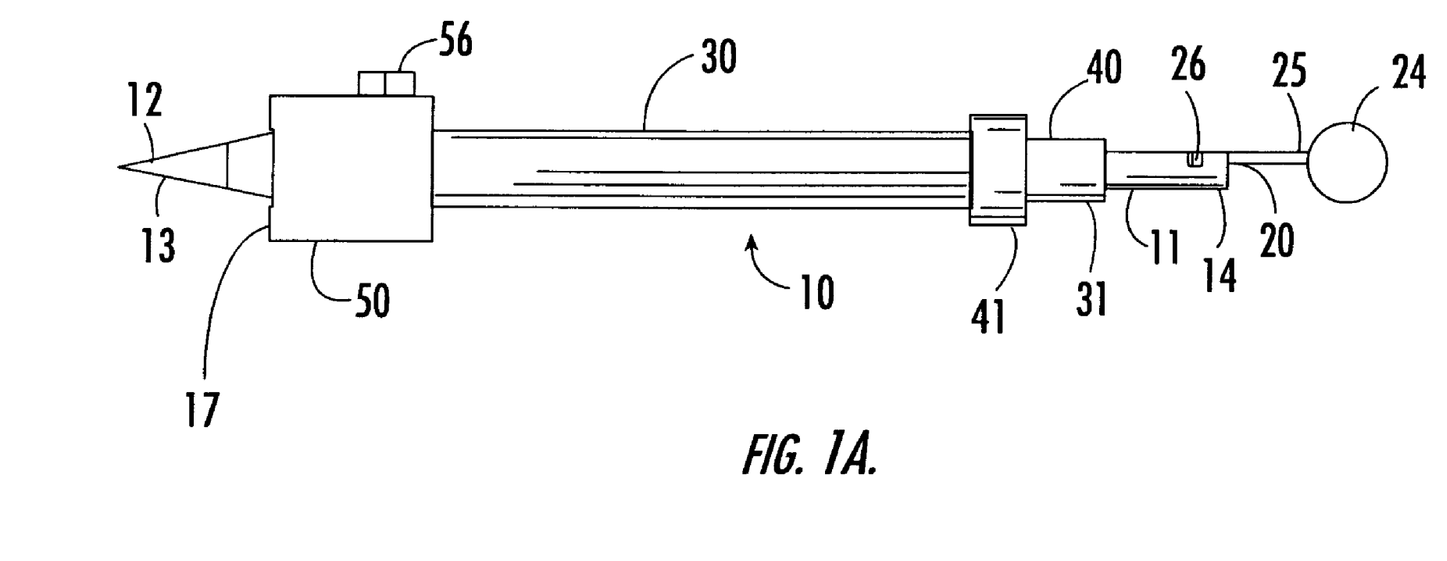
FIG. 1A is a perspective view of the apparatus of the present invention.
Figure 1B:
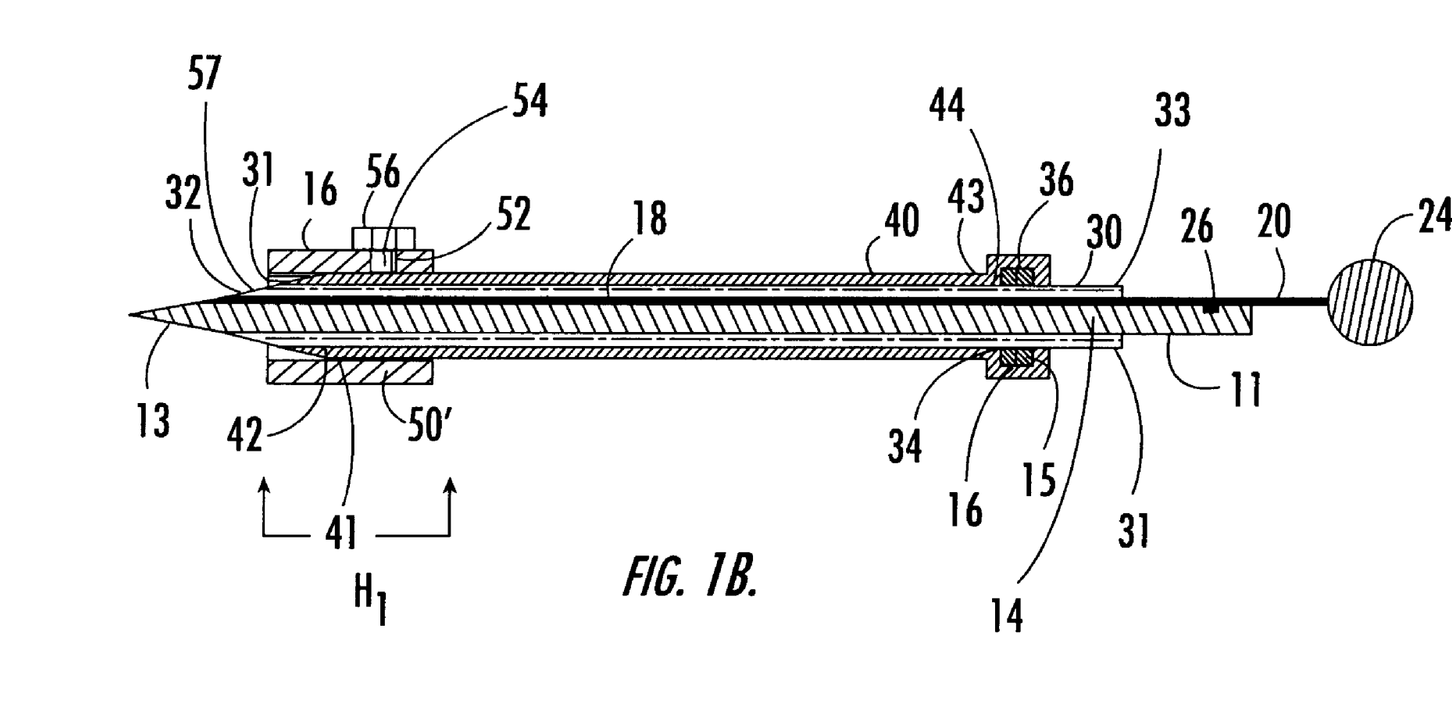
FIG. 1B is a longitudinal cross section of the apparatus of the present invention.

FIG. 1A and FIG. 1B illustrate percutaneous device 10 of the present invention which includes cylinder 11 having distal end 12 in a cone shape 13. Proximal end 14 of cylinder 11 includes external threads 15. Extension 16 extends from proximal end 14 of cylinder 11, thereby providing a handle for insertion and withdrawal of cylinder 11. Cylinder 11 has longitudinal groove 18 which begins at base 17 of cone shape 13 of distal end 12 and ends at proximal end 14.

Figure 2:
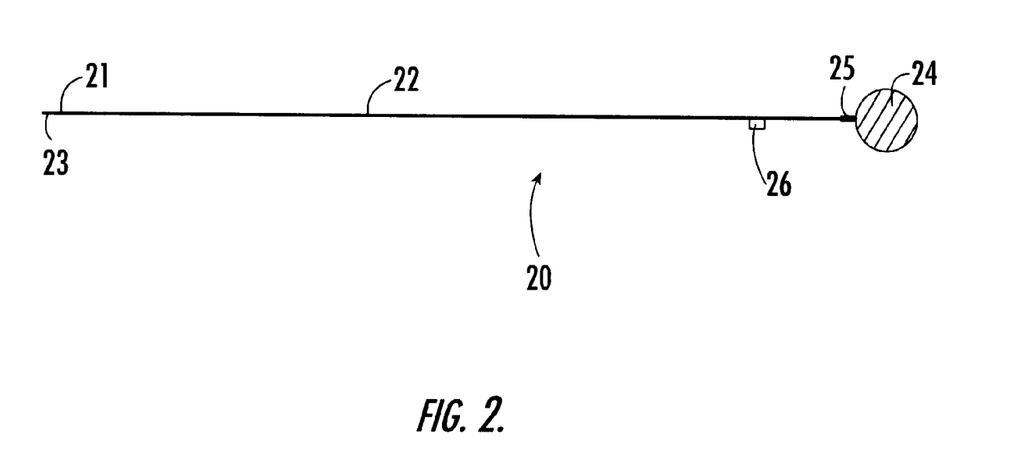
FIG. 2 is a longitudinal cross section of the control rod of the apparatus of the present invention.

Control system 20 is inserted into longitudinal groove 18, as shown in FIG. 2. Control system 20 includes rod 22. Distal end 21 of rod 22 has a rounded end 23. Handle 24 is attached to proximal end 25 of rod 22 for providing maneuvering of rod 22. Rod 22 is fastened to cylinder 11 with brake plate 26. Control system 20 verifies that cone shape 13 of cylinder 11 is inserted into the tracheal lumen.

Coaxially over cylinder 11 is hollow interior cylinder 30, as shown in FIG. 1A and 1B. Distal end 31 of hollow interior cylinder 30 is open in a frustum of cone shape 32. Proximal end 33 of hollow interior cylinder 30 includes internal threads 34 and external threads 36.

Coaxially over hollow interior cylinder 30 is hollow exterior cylinder 40. Distal end 41 of hollow exterior cylinder 40 is open in a frustum of cone shape 42. Proximal end 43 of hollow exterior cylinder 40 includes internal threads 44. Internal threads 34 of hollow interior cylinder 30 are fastened to external threads 15 of cylinder 11. External threads 36 of hollow interior cylinder 30 are fastened to internal threads 44 of hollow exterior cylinder 40. In its initial phase, cylinder 11, hollow interior cylinder 30 and hollow exterior cylinder 40 that make up device 10 is a perfect cone at its distal end. Hollow interior cylinder 30 can be released from hollow exterior cylinder 40 and cylinder 11 when cylinder 11 is withdrawn from device 10.

Coaxially over hollow exterior cylinder 40 is ring portion 50. Ring portion 50 includes a segment of a cylinder 52 and threaded groove 54. Segment of a cylinder 52 has a height $H_1$ of about 3 mm to about 4 mm. Ring portion 50 can be fastened to hollow exterior cylinder 40 with screw 56. Hollow exterior cylinder 40 is provided at distal end 41 with notch 57 which indicates a desired location for ring portion 50 at the moment of the initial insertion of cone shape 13 into the tracheal lumen. For example, the thickness of the skin and subcutaneous tissue can be determined through palpation. Ring portion 50 is used for stopping uncontrolled insertion of device 10 into the patient's trachea. Ring portion 50 can be easily adjusted according to the thickness of skin and subjacent layers of the patient by sliding over hollow exterior cylinder 40 to the desired position, thereby ensuring and guarantying the initial insertion of device 10 without any risk of puncturing the posterior wall of the trachea lumen.

Figure 3:
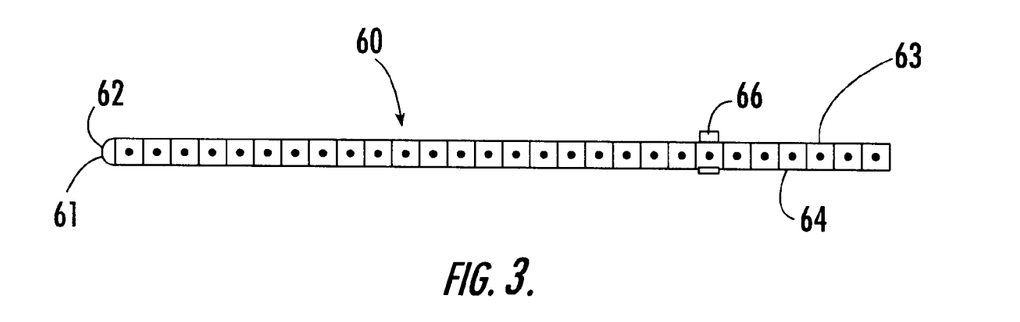
FIG. 3 is a longitudinal cross section of a cylinder with a hemispheric extremity of the apparatus of the present invention.

FIG. 3 shows compact cylinder 60. Compact cylinder 60 includes distal end 61 having a hemisphere shape 62. Extension 63 at proximal end 64 of compact cylinder 60 provides a handle for allowing the insertion and the withdrawal of compact cylinder 60 from device 10. Proximal end 64 has exterior threads 66. Compact cylinder 60 is inserted coaxially into hollow interior cylinder 30 of device 10 after withdrawal of cylinder 11. Exterior threads 66 secure compact cylinder 60 to internal threads 34 of hollow interior cylinder 30. Compact cylinder 60 provides the complete safe forward movement of device 10 all the way to the posterior tracheal wall excluding any risk of injury.

Figure 4:
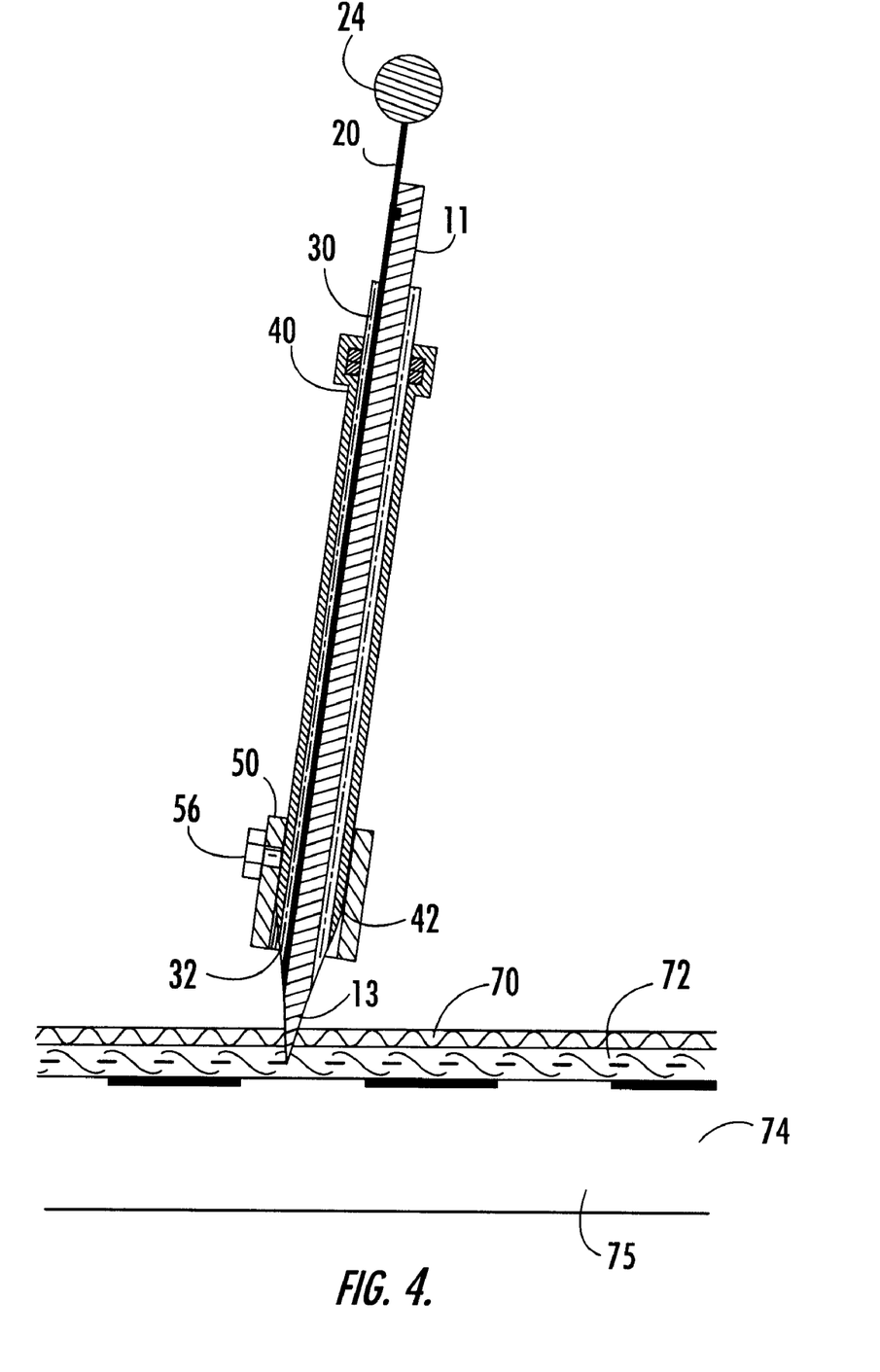
FIGS. 4–9 are sectional cross longitudinal profiles of the apparatus of the present invention showing the insertion into the tracheal lumen.

FIGS. 4–9 show device 10 in operation starting with the puncturing of skin 70 and ending with the insertion of breathing tube 80. FIG. 4 shows ring 50 fastened with screw 56 over hollow exterior cylinder 40 at a position of about 5 mm from distal end 12 of cylinder 11. Skin 70 and the subjacent tissues are punctured with a rotating movement about 45° towards the right and about 45° towards the left while applying continuous pressure.

Figure 5:
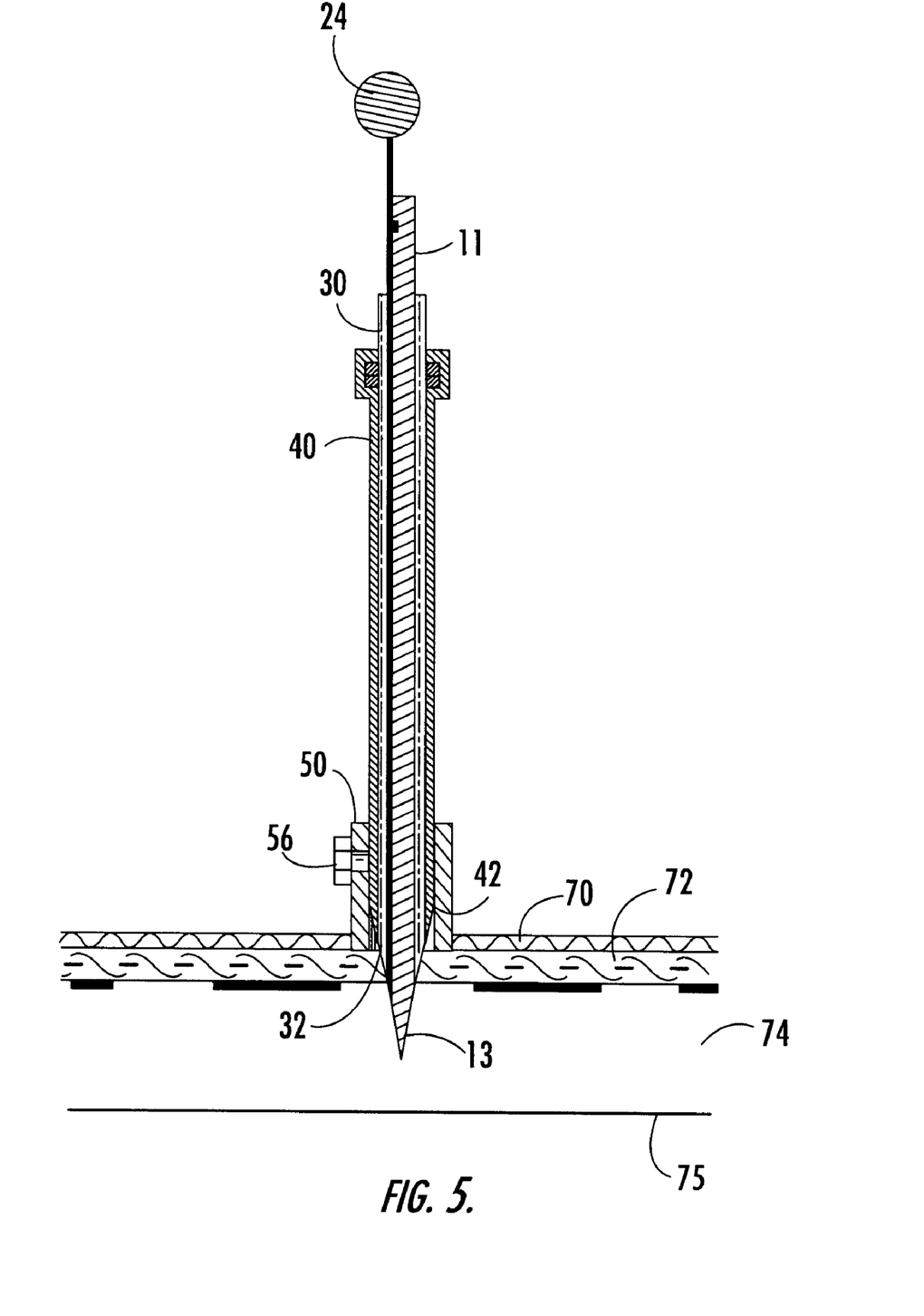
Figure 6:
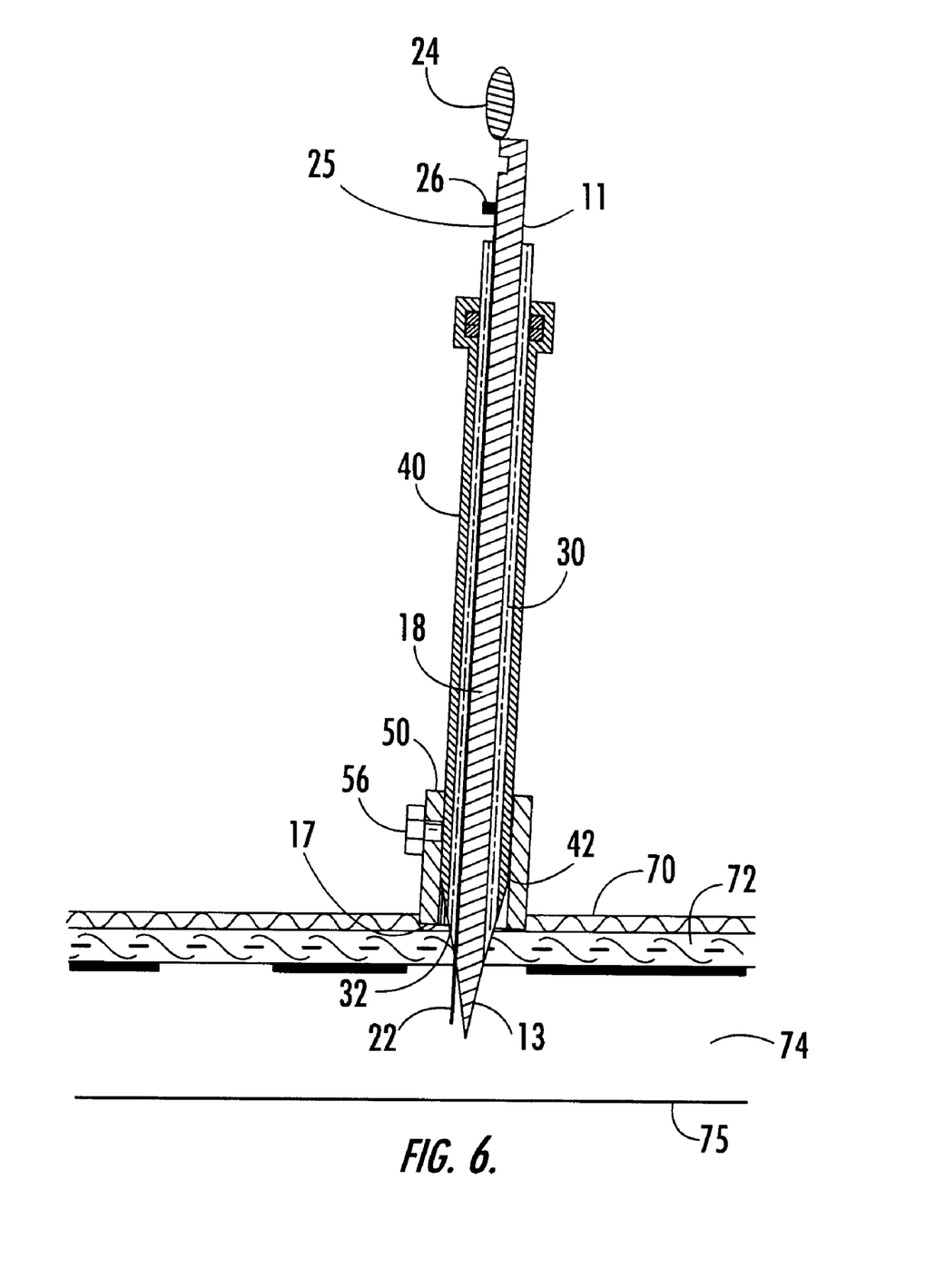

FIG. 5 illustrates penetration of distal end 12 of cylinder 11 through the inter-cartilaginous membrane 72 at which point a feeling of a cardboard resistance is perceived. Thereafter, it is verified with control system 20 that base 17 of cone shape 13 is present into tracheal lumen 74, as shown in FIG. 6. Handle 24 is moved towards left or right for turning brake plate 26 and releasing proximal end 25 of rod 22 after which rod 22 is slidably moved forward into longitudinal groove 18. If a slight resistance is felt during forward movement of rod 22, base 17 of cone 13 is not yet into tracheal lumen 74. If no resistance is felt at distal end 21 of rod 22, the base of cone shape 13 is in tracheal lumen 74. This verification has the advantage of verifying that the next phase of the procedure, the insertion of compact cylinder 60 into tracheal lumen 74 can be performed. If by accident rod 22 comes out of longitudinal groove 18 under no circumstances can it injure posterior tracheal wall 75 because the forward movement of brake plate 26 is blocked by proximal end 33 of hollow interior cylinder 30. Once the presence of base 17 of cone shape 13 is secured into tracheal lumen 74, cylinder 11 and rod 22 are simultaneously unscrewed and withdrawn.

Figure 7A:
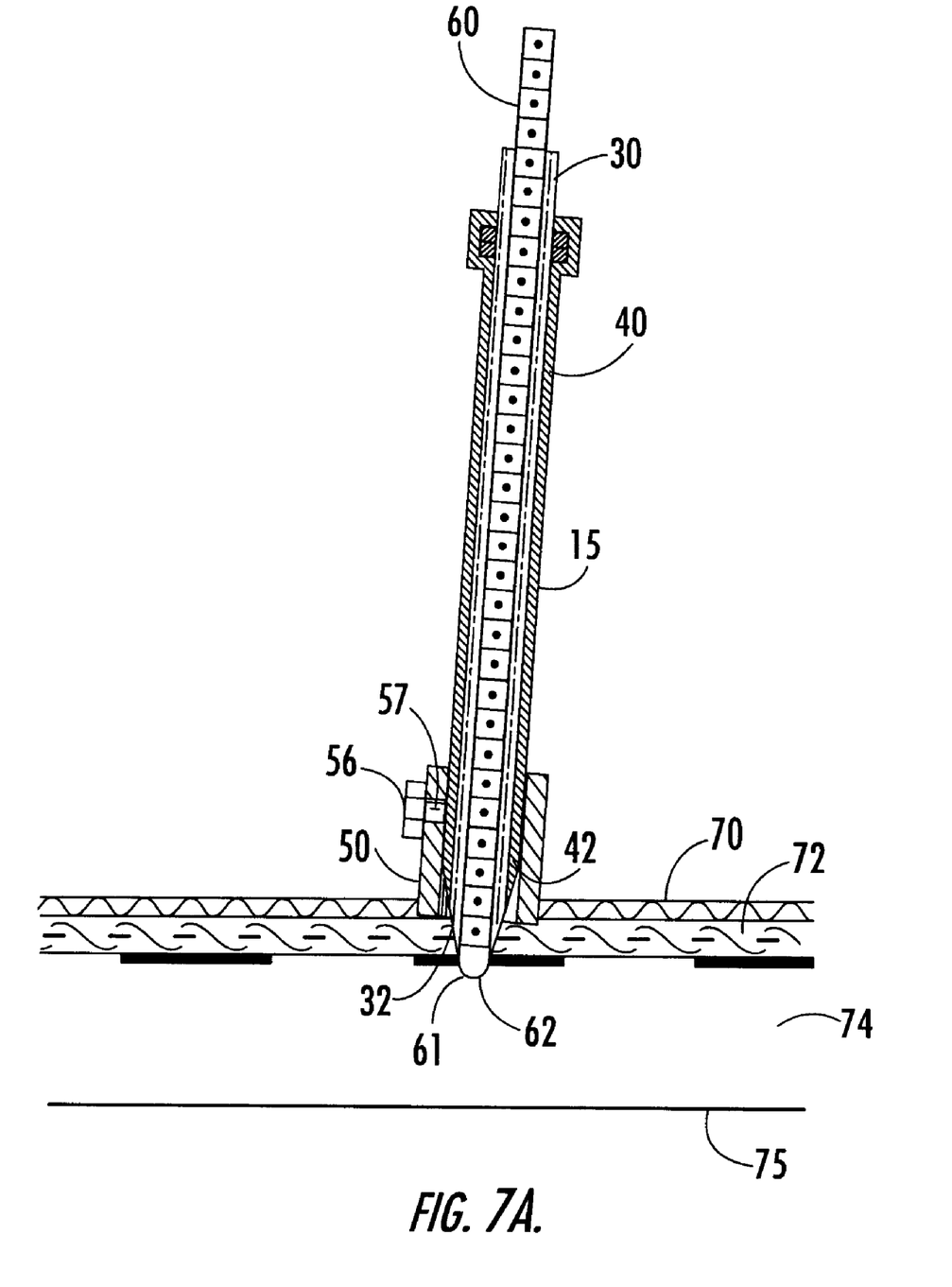
Figure 7B:
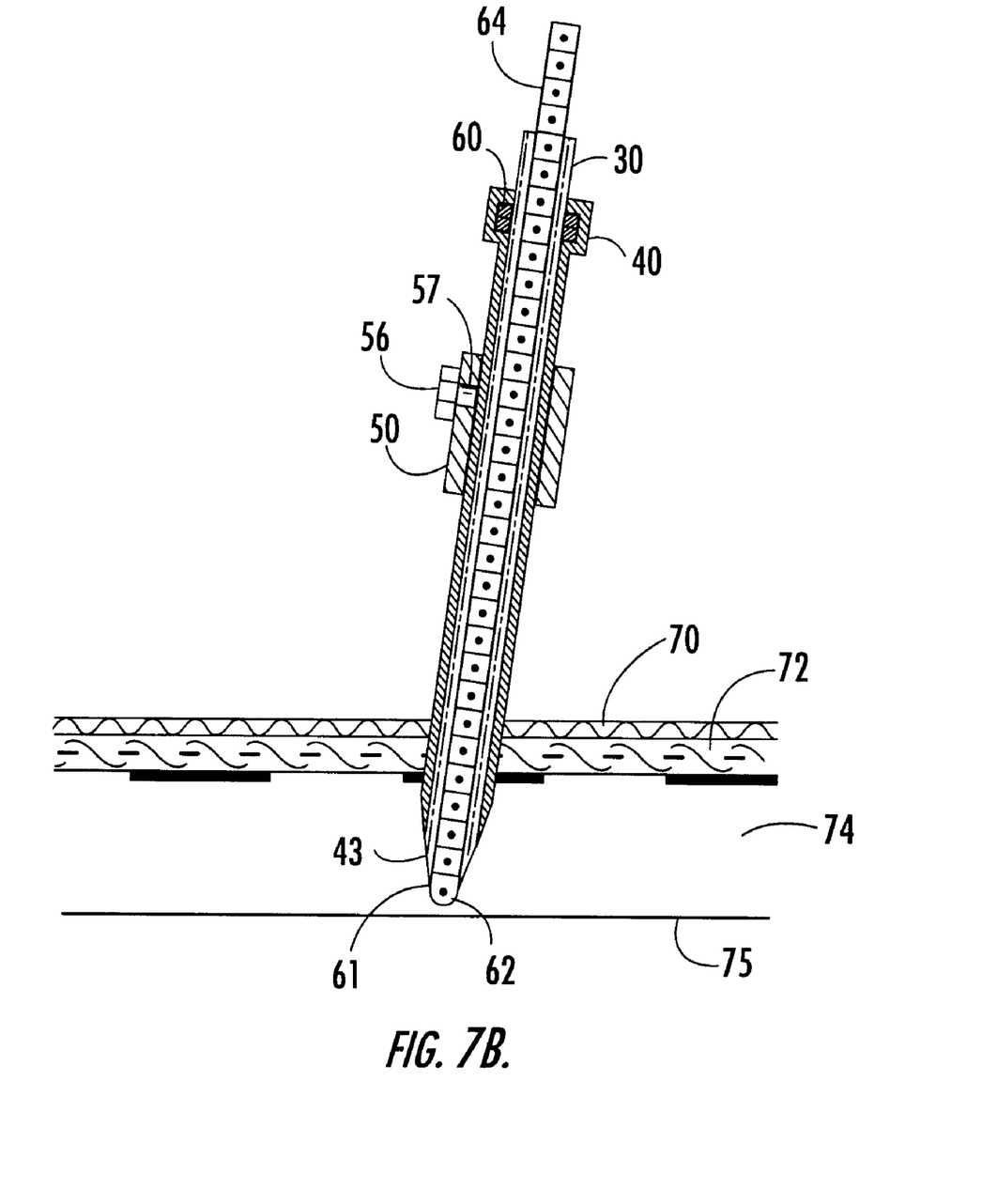

Compact cylinder 60 is inserted into hollow interior cylinder 30, as shown in FIG. 7A. Ring portion 50 is withdrawn by releasing screw 56 and sliding ring portion 50 towards proximal end 43 of hollow exterior cylinder 40, as shown in FIG. 7B.

The forward movement of device 10 continues by application of slight pressure and rotating movement 45° towards right and 45° towards left; when resistance on device 10 is felt when hemisphere shape 62 of distal end 61 of compact cylinder 60 has reached posterior wall 75 of trachea lumen 74; because of the shape of distal end 61 no injury is possible to the posterior wall 75 of the trachea.

Figure 8:
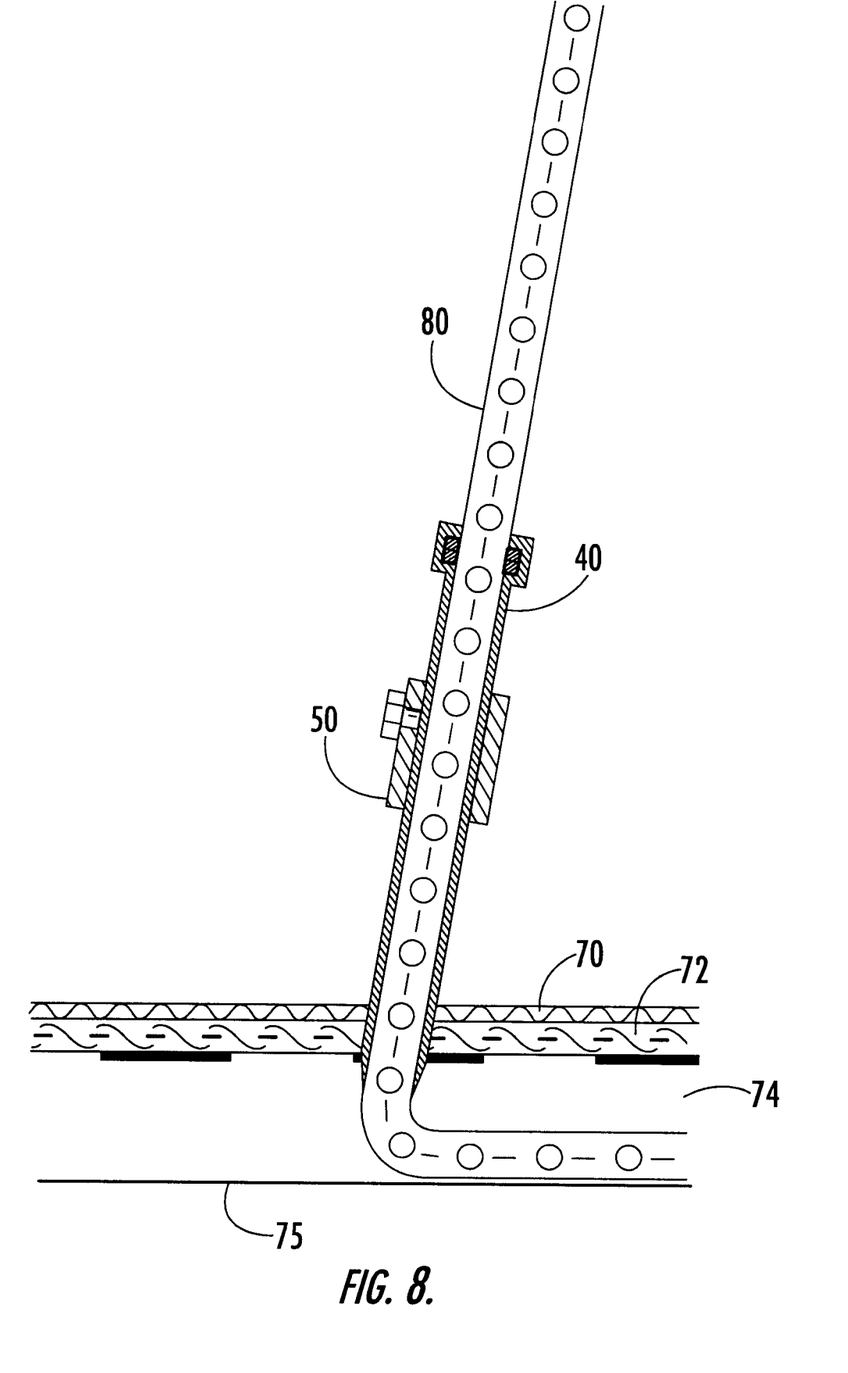

Distal end 61 of compact cylinder 60 once it reaches posterior wall 75 of the trachea lumen 74 brings proximal end 43 of hollow exterior cylinder 40 into tracheal lumen 74. Compact cylinder 60 and hollow interior cylinder 30 are unscrewed and simultaneously withdrawn from device 10 followed by the insertion of breathing tube 80 inside hollow exterior cylinder 40, as shown in FIG. 8.

Figure 9:
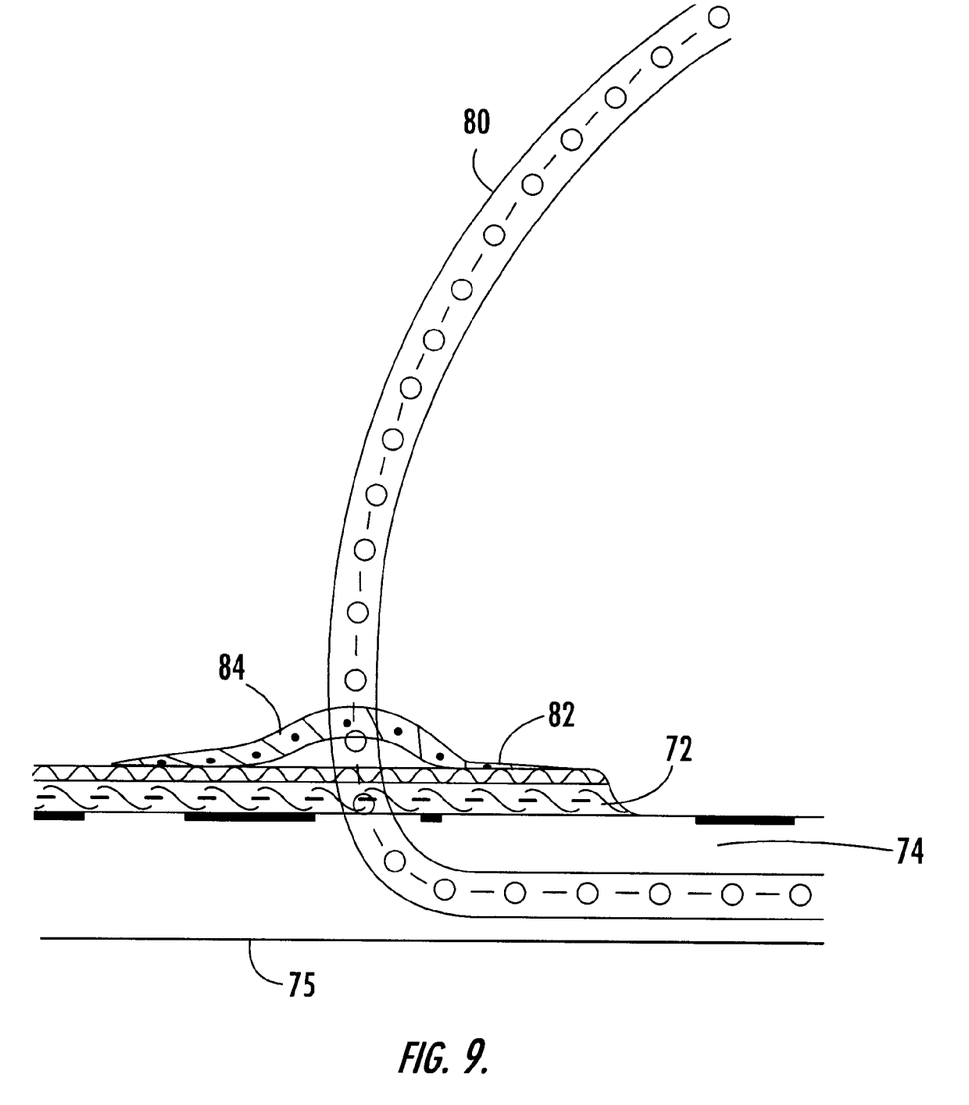

After insertion of breathing tube 80, hollow exterior cylinder 40 is withdrawn using rotating movements, as shown in FIG. 9. In place in trachea lumen 74 remains breathing tube 80 which can be attached to an oxygen source (not shown). Breathing tube 80 is made of a conventional flexible material and is secured in place in exterior cervical area 82 with a conventional bandage 84.

It is to be understood that the above-described embodiments are illustrative of only a few of the many possible specific embodiments which can represent applications of the principles of the invention. Numerous and varied other arrangements can be readily devised in accordance with these principles by those skilled in the art without departing from the spirit and scope of the invention.

What is claimed is:

1. A percutaneous device for performing of a tracheostomy comprising:
    a first cylinder having a distal end in a shape of a cone and a proximal end including an extension;
    a hollow interior cylinder slidable over said first cylinder, said hollow interior cylinder having a distal end in a shape of a frustum of a cone and a proximal end including an extension;
    a hollow exterior cylinder slidable over said hollow interior cylinder, said hollow exterior cylinder having a distal end in a shape of a frustum of a cone and having a proximal end including an extension, said cone of a said first cylinder and said cone of said hollow interior cylinder for initially penetrating the tracheal lumen;
    a second cylinder having a distal end in the shape of a hemisphere and having a proximal end including an extension, said second cylinder for being slidable within said hollow interior cylinder upon removal of said first cylinder after said cone of said first cylinder and said cone of said hollow interior cylinder initially penetrates the tracheal lumen, wherein said second cylinder, said hollow exterior cylinder and said hollow interior cylinder completing penetration of the tracheal lumen; and
    a breathing tube slidably positioned within said hollow external cylinder upon removal of said second cylinder for insertion into the trachea.

2. The percutaneous device of claim 1 wherein said first cylinder further comprises a longitudinal groove between said distal end and said proximal end of said first cylinder and said device further comprising:
    a control rod slidably positioned in said longitudinal groove, said control rod having a distal end having a rounded end and a proximal end having a handle, said distal end being slidable into the tracheal lumen if said first cylinder has penetrated said tracheal lumen, thereby providing a verification that said first cylinder has penetrated said tracheal lumen.

3. The percutaneous device of claim 2 further comprising:
    a brake plate attached to said control rod, said break plate being received in a stop notch of said longitudinal groove, said stop notch positioned at a predetermined distance in said longitudinal groove, thereby controlling the insertion of said control rod to said predetermined distance.

4. The percutaneous device of claim 1 further comprising:
    a ring portion slidably received over said hollow exterior cylinder and positioned at a desired position along said hollow exterior cylinder thereby said ring preventing said device from penetrating into said tracheal lumen beyond said ring.

5. The percutaneous device of claim 4 wherein said ring has a height of about 3 mm to about 4 mm.

6. The percutaneous device of claim 4 wherein said hollow external cylinder includes a stop notch for indicating said desired position in an initial phase of penetration.

7. The percutaneous device of claim 6, further comprising:
    fastening means for fastening said ring in said desired position.

8. The percutaneous device of claim 7 wherein said fastening means comprises a screw.

9. The percutaneous device of claim 1 further comprising means for attaching said first cylinder to said hollow interior cylinder.

10. The percutaneous device of claim 9 wherein means for attaching said first cylinder to said hollow interior cylinder comprises:
    external threads formed on said proximal end of said first cylinder and internal threads formed on said proximal end of said hollow interior cylinder.

11. The percutaneous device of claim 1 further comprising:
    means for attaching said hollow interior cylinder to said hollow exterior cylinder.

12. The percutaneous device of claim 11 wherein means for attaching said hollow interior cylinder to said hollow exterior cylinder comprises:
    external threads formed on said proximal end of said hollow interior cylinder and internal threads formed on said proximal end of said external hollow cylinder.

13. The percutaneous device of claim 1 further comprising:
    means for attaching said second cylinder to said hollow interior cylinder.

14. The percutaneous device of claim 13 wherein means for attaching said second cylinder to said hollow interior cylinder comprises:
    external threads formed on said proximal end of said second cylinder and internal threads formed on said proximal end of said hollow interior cylinder.

15. A method for performing of a tracheostomy comprising the steps of:
    inserting a first cylinder having a distal end in a shape of a cone and a proximal end including an extension, a hollow interior cylinder slidable over said first cylinder, said hollow interior cylinder having a distal end in a shape of a frustum of a cone and a proximal end including an extension; and a hollow exterior cylinder slidable over said hollow interior cylinder, said hollow exterior cylinder having a distal end in a shape of a frustum of a cone and having a proximal end including an extension, said cone of a said first cylinder and said cone of said hollow interior cylinder for initially penetrating the tracheal lumen;

removing said first cylinder from said hollow interior cylinder after cone of said hollow interior cylinder initially penetrates the tracheal lumen;

inserting a second cylinder having a distal end in the shape of a hemisphere and having a proximal end including an extension, said second cylinder for being slidable within said hollow interior cylinder said second cylinder, said hollow exterior cylinder and said hollow interior cylinder completing penetration of the tracheal lumen;

removing said second cylinder simultaneously with said hollow interior cylinder from said hollow exterior cylinder; and inserting a breathing tube slidably positioned within said hollow external cylinder upon removal of said second cylinder and said hollow interior cylinder for insertion into the trachea.

* * * * *